United States Patent
Kurimoto et al.

(10) Patent No.: US 6,469,200 B1
(45) Date of Patent: Oct. 22, 2002

(54) PROCESS FOR PRODUCING 2-ALKYLIDENE-4-BROMOACETOACETIC ACID ESTER

(75) Inventors: Isao Kurimoto, Suita (JP); Akihiko Nakamura, Takatsuki (JP); Norihiko Hirata, Suita (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/429,083

(22) Filed: Oct. 29, 1999

(30) Foreign Application Priority Data

Nov. 2, 1998 (JP) .............................. 10-311939

(51) Int. Cl.⁷ .................. C07C 69/76; C07C 69/66; C07C 69/72
(52) U.S. Cl. .................. 560/174; 560/178; 560/53
(58) Field of Search ................ 560/53, 174, 178

(56) References Cited

U.S. PATENT DOCUMENTS

| 4,416,880 A | * 11/1983 | Boberg et al. ............... 424/246 |
| 4,943,568 A | * 7/1990 | Boberg et al. ............... 514/206 |
| 5,214,037 A | * 5/1993 | Kubota et al. ............... 514/206 |
| 5,352,792 A | * 10/1994 | Kubota et al. ............... 548/255 |

FOREIGN PATENT DOCUMENTS

| EP | 0212340 B1 | 3/1987 |
| EP | 0421752 A2 | 4/1991 |
| EP | 0329457 | * 1/1992 |
| EP | 0467647 B1 | 1/1992 |
| EP | 0467647 A2 | * 1/1992 |
| EP | 1000939 A1 | * 5/2000 |
| JP | 2618119 B2 | 3/1993 |

OTHER PUBLICATIONS

Kawano, Yoshinobu et al. *Journal of Fermentation and Bioengineering*, vol. 78, No. 4, pp. 293–297, (1994).

* cited by examiner

Primary Examiner—Alan L. Rotman
Assistant Examiner—Taylor V. Oh
(74) Attorney, Agent, or Firm—Birch, Stewart, Kolasch & Birch, LLP

(57) ABSTRACT

A process for producing a 2-alkylidene-4-bromoacetoacetic acid ester of the formula (3):

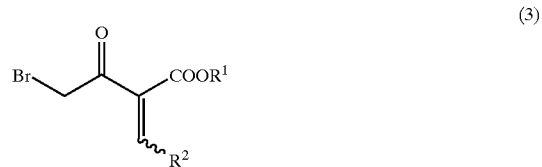

(3)

wherein $R^1$ and $R^2$ each independently represent a lower alkyl group having 1–5 carbon atoms, the process is characterized by reacting a 4-bromoacetoacetic acid ester of the formula (1):

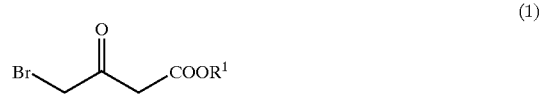

(1)

where $R^1$ has the same meaning as defined above, with an aldehyde of the formula (2):

$$R^2CHO \qquad (2)$$

wherein $R^2$ has the same meaning as defined above, in an inert organic solvent in the presence of an amine and a carboxylic acid.

11 Claims, No Drawings

PROCESS FOR PRODUCING 2-ALKYLIDENE-4-BROMOACETOACETIC ACID ESTER

FIELD OF THE INVENTION

The present invention relates to a process for producing a 25 alkylidene-4-bromoacetoacetic acid ester that is useful as an intermediate of pharmaceuticals, specifically, as an intermediate of a side chain part of antibiotics disclosed in Japanese Patent No. 2618119.

DESCRIPTION OF THE RELATED ART

In the Japanese Patent No. 2618119 there is disclosed a process for producing a 2-alkylidene-4-bromoacetoacetic acid ester in which process methyl 2-propylidene-4-chloroacetoacetate is subjected to a halogen exchange reaction with sodium bromide, wherein said methyl 2-propylidene-4-chloroacetoacetate was obtained by condensing methyl 4-chloroacetoacetate and propionaldehyde by using piperidine and acetic acid as catalysts.

This process, however, is not always satisfactory in that it requires a halogen exchange reaction wherein the conversion ratio is not satisfactory and expensive methyl 4-chloroacetoacetate is required. Hence, new production processes have been desired.

SUMMARY OF THE INVENTION

An object of the Invention is to provide a process which can provide the desired 2-alkylidene-4-bromoacetoacetic acid ester by using, as a starting material, a 4-bromoacetoacetic acid ester which can be readily derived from an acetoacetic acid ester in a good yield in an industrial scale.

The present invention provides:
a process for producing a 2-alkylidene-4-bromoacetoacetic acid ester of the formula (3):

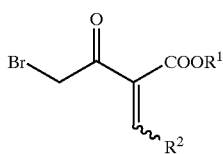

(3)

wherein $R^1$ and $R^2$ each independently represent a lower alkyl group having 1–5 carbon atoms, which comprises:
reacting a 4-bromoacetoacetic acid ester of the formula (1):

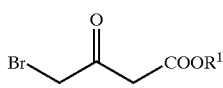

(1)

wherein $R^1$ has the same meaning as defined above, with an aldehyde of the formula (2):

$R^2CHO$  (2)

wherein $R^2$ has the same meaning as defined above, in an inert organic solvent in the presence of an amine and a carboxylic acid.

DESCRIPTION OF THE PREFERRED EMBODIMENTS

The 4-bromoacetoacetic acid ester of the formula (1) used in the present invention, can be readily prepared by reacting an acetoacetic acid ester of the formula (4):

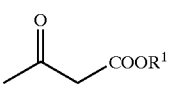

(4)

wherein $R^1$ has the same meaning as defined above, with bromine in the presence of an organic solvent according to the method disclosed in J. Org. Chem., 12, 342 (1947), Helvetica Chemica Acta, 66, 1475 (1983), or the like.

Although the 4-bromoacetoacetic acid ester prepared in the above-described method may be used as a starting material in the present invention after being purified by distillation or the like, a concentrated reaction mixture obtained by a partial or total evaporation of the solvent from the reaction mixture may be used as it is without purification.

Examples of the lower alkyl group having 1 to 5 carbon atoms for $R^1$ in the 4-bromoacetoacetic acid ester of the formula (1) include a methyl group, an ethyl group, a n-propyl group, an i-propyl group, a n-butyl group, a t-butyl group and a n-pentyl group Specific examples of the 4-bromoacetoacetic acid ester of the formula (1) include methyl 4-bromoacetoacetate, ethyl 4-bromoacetoacetate, n-propyl 4-bromoacetoacetate, i-propyl 4-bromoacetoacetate, n-butyl 4-bromoacetoacetate, t-butyl 4-bromoacetoacetate, n-pentyl 4-bromoacetoacetate, and the like.

Examples of the lower alkyl group having 1 to 5 carbon atoms for $R^2$ in the aldehyde of the formula (2) in the present invention include a methyl group, an ethyl group, a n-propyl group, an i-propyl group, a n-butyl group, a t-butyl group and a n-pentyl group.

Specific examples of the aldehyde of the formula (2) include acetaldehyde, propionaldehyde, butylaldehyde, isobutylaldehyde, valeraldehyde, trimethylacetaldehyde, hexanal, and the like.

The amount of the aldehyde to be used of the formula (2) is usually 1 to 10 moles, preferably 1.2 to 5 moles per mol of the 4-bromoacetoacetic acid ester of the formula (1).

The reaction of the present invention is carried out in the presence of an amine and a carboxylic acid as catalysts. Specific examples of the amine include:
primary amines, for example, ammonia, a $(C_1-C_{20})$ alkylamine (e.g., methylamine, ethylamine and n-propylamine),
secondary amines, for example, a di$(C_1-C_{20})$alkylamine, which alkyl may be the same or different and may contain a heteroatom such as oxygen or nitrogen(e.g., dimethylamine, diethylamine, piperidine and morpholine), tertiary amines, for example, a tri $(C_1-C_{20})$alkylamine, which alkyl may be the same or different, (e.g., triethylamine) and a $(C_5-C_9)$aromatic tertiary amine (e.g., pyridine) and mixtures thereof. The secondary amines are preferably used.

Specific examples of the carboxylic acid include a $(C_2-C_6)$alkanoic acid such as acetic acid, propionic acid, butyric acid, valeric acid, caproic acid and mixtures thereof.

The amount of the amine to be used is usually 0.001 to 1 mole, preferably 0.01 to 0.5 mol per mol of the 4-bromoacetoacetic acid ester of the formula (1).

The amount of the carboxylic acid to be used is usually 0.1 to 10 moles, preferably 0.5 to 5 moles per mol of the amine.

The reaction is usually carried out in an inert organic solvent. Such an inert organic solvent is not particularly limited unless it affects the reaction adversely. Specific examples thereof include aromatic hydrocarbons such as toluene, benzene and xylene, aliphatic hydrocarbons such as hexane and heptane, halogenated hydrocarbons such as dichloromethane, dichloroethane, chloroform, 1-chlorobutane and chlorobenzene, ethers such as diethyl ether, t-butyl methyl ether and tetrahydrofuran, ketones such as methyl ethyl ketone and methyl isobutyl ketone, etc.

These organic solvents may be used alone or as a mixture of two or more of them. The amount of the inert organic solvent to be used is not particularly limited and is usually in 0.5 to 100 parts, preferably 1 to 30 parts per 1 part by weight of the 4-bromoacetoacetic acid ester of the formula (1).

The reaction temperature is usually in the range of −80 to 30° C., preferably in the range of −50 to 0° C.

The way to feed the starting materials and catalysts for the reaction is important in order to control side reactions such as self-condensation of the aldehyde of the formula (2), and the like and to achieve good yield.

The reaction can usually be conducted by adding the amine to a solution of the 4-bromoacetoacetic acid ester of the formula (1), the aldehyde of the formula (2) and the carboxylic acid in an inert organic solvent.

Alternatively it may be preferably conducted in the following manner which advantageously facilitates the control of the reaction temperature of the exothermic reaction from industrial viewpoint:

the reaction can be conducted by adding in parallel the 4-bromoacetoacetic acid ester of the general formula (1), the aldehyde of the formula (2) and the amine to a solution of the carboxylic acid catalyst in the inert organic solvent; or the reaction is conducted by adding the 4-bromoacetoacetic acid ester of the formula (1), the aldehyde of the formula (2), the amine and carboxylic acid in parallel to an inert organic solvent.

After completion of the reaction, the reaction mixture is, for example, washed with an aqueous acid solution, water and the like and the solvent is concentrated to give the desired 2-alkylidene-4-bromoacetoacetic acid ester of the formula (3). The solution of 2-alkylidene-4-bromoacetoacetic acid ester of the formula (3) after washing is preferably used as it is.

According to the process of the present invention, a 2-alkylidene-4-bromoacetoacetic acid ester that is useful as intermediates of pharmaceuticals and the like can be produced in good yield and advantageously from industrial view point.

EXAMPLES

The following examples illustrates the present invention in detail, however the present invention is not limited thereto.

Production Example of Methyl 4-Bromoacetoacetate 1

In 679 g of dichloromethane was dissolved 116 g of methyl acetoacetate and cooled to −5° C. To this mixture was dropwise added 160 g of bromine at 0 to 5° C. over a period of one hour. The mixture was kept at that temperature for one hour, followed by being heated to 20° C. and kept at that temperature for two hours. After blowing air to the reaction mixture for one hour, concentrating the mixture in vacuous gave 212 g of oil residue. Distillation of this oil residue under reduced pressure gave 54.5 g of methyl 4-bromoacetoacetate having a purity of 95.6%.

Production Example of Methyl 4-Bromoacetoacetate 2

In 2613 g of 1-chlorobutane was dissolved 523 g of methyl acetoacetate and cooled to 0° C. To this mixture was dropwise added 719 g of bromine at 5±5° C. over a period of one hour, and the mixture was thereafter kept at that temperature for four hours. The reaction mixture was washed with 1161 g of a 10% saline solution. After separating the mixture into an aqueous and organic layers, concentration of the organic layer in vacuous at a temperature of 40° C. or less gave 782.9 g of crude methyl 4-bromoacetoacetate. The gas chromatography analysis indicated that the content of methyl 4-bromoacetoacetate in the crude product was 72% (564 g, 64% yield).

Example 1

In 34 g of dichloromethane were dissolved 5.0 g (pure weight: 4.78 g) of methyl 4-bromoacetoacetate obtained in Production Example 1, 2.23 g of propionaldehyde and 0.15 g of acetic acid, and cooled to −30° C. To the mixture was dropwise added a mixed solution of 0.26 g of piperidine and 1.18 g of dichloromethane at −27±2° C. over a period of 30 minutes. After keeping at that temperature for 3.5 hours, 15 g of a 0.7% aqueous hydrochloric acid was added to the reaction mixture and heated to 3° C. The mixture was separated into an aqueous and organic layers. The organic layer was washed with 15 g of a 1% aqueous sodium hydrogen carbonate solution and 15 g of water in this order at 0 to 50° C., and concentrated in vacuous at a temperature of 15° C. or less to yield 8.57 g of a concentrated solution of methyl 2-propylidene-4-bromoacetoacetate. The high-performance liquid chromatography analysis indicated that the concentrated solution contained 5.31 g of methyl 2-propylidene-4-bromoacetoacetate (92.0% yield, E/Z ratio=49/51).

Example 2

A mixed solution of 39.9 g of methyl isobutyl ketone and 2.61 g of acetic acid was cooled to −27° C., and to this solution were dropwise added in parallel 38.1 g (pure weight: 27.43 g) of the crude methyl 4-bromoacetoacetate obtained in Production Example 2, 25.44 g of propionaldehyde and a solution obtained by dissolving 2.30 g of piperidine in 2.63 g of methyl isobutyl ketone at −27±2° C. over a period of 6 hours. After the completion of addition, the mixture was kept at that temperature for 2 hours, and thereafter to the mixture were added 68.85 g of a 1.4% aqueous hydrochloric acid and 85.13 g of methyl isobutyl ketone. The resulting mixture was heated to 3° C. and separated into an aqueous and organic layers. The high-performance liquid chromatography analysis of the organic layer indicated that this layer contained 29.56 g of methyl 21.5 propylidene-4-bromoacetoacetate (89.4% yield, E/Z ratio=54/46).

Example 3

First 39.9 g of methyl isobutyl ketone was cooled to −27° C., and to this were dropwise added in parallel 38.1 g (pure weight: 27.43 g) of the crude methyl 4-bromoacetoacetate obtained in Production Example 2, 25.44 g of propionaldehyde, a solution obtained by dissolving 2.30 g of piperidine in 2.63 g of methyl isobutyl ketone, and 2.61 g of acetic acid at −27±2° C. over a period of 6 hours. After the completion of the addition, the mixture was kept at that temperature for 2 hours, and thereafter to the mixture were added 68.85 g of a 1.4% aqueous hydrochloric acid and 85.13 g of methyl isobutyl ketone. The temperature of the resulting mixture was raised to 3° C. and separated into an aqueous and organic layers. The high-performance liquid chromatography analysis of the organic layer indicated that this layer contained 29.56 g of methyl 2-propylidene-4-bromoacetoacetate (88.2% yield, E/Z ratio=53/47).

Production Example of Methyl 4-Bromoacetoacetate 3

22.7 kg of methyl acetoacetate was dissolved in 113.3 kg of 1-chlorobutane and cooled to 0° C. To this mixture was added dropwise 31.4 kg of bromine at 5° C. over 2 hours, and the mixture was thereafter kept at that temperature for 8 hours. The reaction mixture was cooled to −10° C. and added dropwise to 22.7 kg of water at a temperature 10° C. or less in 2 hours, then washed and separated to give an organic layer. The obtained organic layers were concentrated under reduced pressure at a temperature of 40° C. or less to give 42.0 kg of crude methyl 4-bromoacetoacetate. The gas chromatography analysis indicated that the content of methyl 4-bromoacetoacetate in the crude product was 65.3% (27.4 kg, 72% yield), wherein the content of 1-chlorobutane was 19.7%.

Example 4

38.0 kg of crude methyl 4-bromoacetoacetate obtained in Production Example 3 containing 24.8 kg of said compound, 16.5 kg of propinaldehyde and 1.22 kg of piperidine were simultaneously dropwise added at −24±3° C. over 9 hours to a mixed solution of 28.6 kg of 1-chlorobutane and 2.55 kg of acetic acid pre-cooled to −27° C., and resulting solution was kept at the temperature for 3 hours. Then the reaction mixture was added to 36.1 kg of 1.4% hydrochloric acid and separated. 78.8 kg of the obtained organic layer was analyzed by high performance liquid chromatography, which showed the content of methyl 2-propylidene-4-bromoacetoacetate was 25.9 kg (86.6% yield, E/Z ratio=55/45).

Comparative Example 1

In 16.98 g of methyl isobutyl ketone were dissolved 12.04 g of methyl 4-chloroacetoacetate, 6.97 g of propionaldehyde and 0.48 g of acetic acid, and the mixture was cooled to −30° C. To the resulting solution was dropwise added a mixed solution of 0.41 g of piperidine and 0.54 g of methyl isobutyl ketone at −27±2° C. over a period of 30 minutes. After keeping at that temperature for 3 hours, to the resulting solution was added 48 g of a 0.35% aqueous hydrochloric acid and heated to 3° C., and thereafter the mixture was separated into an aqueous and organic layers. The organic layer was washed with 48 g of a 1% aqueous sodium hydrogencarbonate solution and 48 g of water in this order at 0 to 5° C., and concentrated in vacuo at a temperature of 15° C. or less to yield 31.17 g of a concentrated solution of methyl 2-propylidene-4-chloroacetoacetate. The high-performance liquid chromatography analysis indicated that the concentrated solution contained 12.44 g of methyl 2-propylidene-4-chloroacetoacetate (81.6% yield, E/Z ratio=46/54).

In 10.23 g of N,N-dimethylformamide was dissolved 11.45 g of the concentrated solution (pure weight of methyl 2-propylidene-4-chloroacetoacetate: 4.57 g), and cooled to 10° C. To this mixture was added 6.17 g of sodium bromide, and thereafter heated to 22° C. and vigorously stirred at 22±2° C. for 2 hours. The resulting reaction solution was cooled to 5° C. and washed with 20 g of water, followed by being separated into an aqueous and organic layers. The high-performance liquid chromatography analysis of the organic layer indicated that this layer contained 4.66 g of methyl 2-propylidene-4-bromoacetoacetate (82.6% yield, E/Z ratio=52/48) and 9.7% of the starting material methyl 2-propylidene-4-chloroacetoacetate remained.

What is claimed is:

1. A process for producing a 2-alkylidene-4-bromoacetoacetic acid ester of the formula (3):

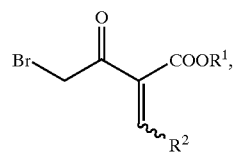

wherein $R^1$ and $R^2$ each independently represent a lower alkyl group having 1–5 carbon atoms, which comprises reacting:

a 4-bromoacetoacetic acid ester of the formula (1):

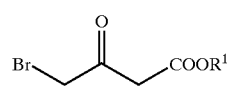

wherein $R^1$ has the same meaning as defined above, with an aldehyde of the formula (2):

$$R^2CHO \qquad (2)$$

wherein $R^2$ has the same meaning as defined above, in an inert organic solvent in the presence of an amine and a carboxylic acid.

2. The process according to claim 1, wherein the 4-bromoacetoacetic acid ester of the formula (1), the aldehyde of the formula (2) and the amine are added in parallel to a solution of the carboxylic acid of the formula (1) in the inert organic solvent.

3. The process according to claim 1, wherein 4-bromoacetoacetic acid ester of the formula (1), the aldehyde of the formula (2), the amine and carboxylic acid are added in parallel to the inert organic solvent.

4. The process according to claim 1, wherein a ($C_1$–$C_{20}$) secondary amine and a ($C_2$–$C_6$) carboxylic acid are used as the amine and carboxylic acid.

5. The process according to claim 4, wherein the secondery amine is piperidine and the carboxylic acid is acetic acid.

6. The process according to claim 1, wherein said lower alkyl group is selected from the group consisting of a methyl group, an ethyl group, a n-propyl group, an i-propyl group, a n-butyl group, a t-butyl group and a n-pentyl group.

7. The process according to claim 1, wherein the amine is selected from a group consisting of-methyl amine, ethylamine, n-propylamine, dimethylamine, diethylamine, piperidine, morpholine, triethylamine, pyridine and combinations thereof.

8. The process according to claim 1, wherein the carboxylic acid is selected from the group consisting of acetic acid, propionic acid, butyric acid, valeric acid, caproic acid and combinations thereof.

9. The process according to claim 1, wherein the inert organic solvent is selected from the group consisting of toluene, benzene, xylene, hexane, heptane, dichloromethane, dichloroethane, chloroform, 1-chlorobutane, chlorobenzene, diethyl ether, t-butyl methyl ether, tetrahydrofuran, methyl ethyl ketone, methyl isobutyl ketone and combination thereof.

10. The process according to claim 1, wherein the reaction uses 1 to 10 moles of the aldehyde of formula (2) per mole of the 4-bromoacetoacetic acid ester of formula (1);

0.001 to 1 moles of the amine per mole of the 4-bromoacetoacetic acid ester of formula (1);

0.1 to 10 moles of the carboxylic acid per mole of the 4-bromoacetoacetic acid ester of formula (1); and 0.5 to 100 parts of the inert organic solvent per 1 part by weight of the 4-bromoacetoacetic acid ester of formula (1).

11. The process according to claim 10, wherein the reaction occurs in a temperature range of −80 to 30° C.

* * * * *

UNITED STATES PATENT AND TRADEMARK OFFICE
CERTIFICATE OF CORRECTION

PATENT NO. : 6,469,200 B1
DATED : October 22, 2002
INVENTOR(S) : Isao Kurimoto et al.

It is certified that error appears in the above-identified patent and that said Letters Patent is hereby corrected as shown below:

<u>Title page,</u>
Item [73], Assignee should read as follows:

-- Sumitomo Chemical Company, Limited, Osaka (JP)
and
Shionogi & Company, Ltd., Osaka (JP) --

Signed and Sealed this

First Day of July, 2003

JAMES E. ROGAN
*Director of the United States Patent and Trademark Office*